US009161918B2

(12) United States Patent
Venkatesh

(10) Patent No.: US 9,161,918 B2
(45) Date of Patent: Oct. 20, 2015

(54) TIMED, PULSATILE RELEASE SYSTEMS

(75) Inventor: Gopi M. Venkatesh, Vandalia, OH (US)

(73) Assignee: Adare Pharmaceuticals, Inc., Lawrenceville, NJ (US)

( * ) Notice: Subject to any disclaimer, the term of this patent is extended or adjusted under 35 U.S.C. 154(b) by 935 days.

(21) Appl. No.: 11/120,139

(22) Filed: May 2, 2005

(65) Prior Publication Data

US 2006/0246134 A1    Nov. 2, 2006

(51) Int. Cl.
*A61K 9/00* (2006.01)
*A61K 9/20* (2006.01)
*A61K 9/50* (2006.01)

(52) U.S. Cl.
CPC ............. *A61K 9/2081* (2013.01); *A61K 9/5042* (2013.01); *A61K 9/5047* (2013.01); *A61K 9/5078* (2013.01); *A61K 9/5084* (2013.01)

(58) Field of Classification Search
CPC .................... A61K 47/48938; A61K 51/1258; A61K 9/2031
See application file for complete search history.

(56) References Cited

U.S. PATENT DOCUMENTS

| | | |
|---|---|---|
| 3,184,386 A | 5/1965 | Stephenson |
| 3,558,768 A | 1/1971 | Klippel |
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |

(Continued)

FOREIGN PATENT DOCUMENTS

| | | |
|---|---|---|
| EP | 0052492 B1 | 2/1984 |
| EP | 0166440 A2 | 1/1986 |

(Continued)

OTHER PUBLICATIONS

Zheng et al., Influence of Eudragit NE 30 D Blended with Eudgragit L 30 D-55 on the Release of Phenylpropanolamine Hydrochloride from Coated Pellets, Drug Development and INdustrial Pharmacy, 2003, 29(3), pp. 357-366.*

(Continued)

*Primary Examiner* — Benjamin Packard
(74) *Attorney, Agent, or Firm* — Cooley LLP

(57) ABSTRACT

A unit multiparticulate dosage form for delivering one or more basic, active pharmaceutical ingredients into the body in need of such medications to achieve target PK (pharmacokinetics) profiles is described. The dosage form comprises one or more multicoated drug particles (beads, pellets, mini-/micro-tablets) having a barrier coating and a lag-time coating. Each Timed Pulsatile Release (TPR) bead population exhibits pre-determined lag-time followed by differing release characteristics. The composition and thickness of the barrier coating, composition and thickness of the lag-time coating, ratio of IR beads to one or more TPR bead populations and total dose may be varied depending on the alkalinity, pH-dependent solubility and elimination half-life of the active ingredients to achieve target PK profiles (suitable for a once or twice daily dosing regimen) in patients in need of such medications.

42 Claims, 3 Drawing Sheets

Timed, Pulsatile-Release Profiles of Nizatidine of Ex. 1C
(No Barrier Coating / Lag-time Coating)

(56) References Cited

U.S. PATENT DOCUMENTS

| | | |
|---|---|---|
| 4,556,678 A | 12/1985 | Hsiao |
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A * | 7/1990 | Mehta ............... 424/495 |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bücheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chauveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A * | 10/2000 | Grimmett et al. ............... 424/471 |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |

(56) References Cited

U.S. PATENT DOCUMENTS

| | | |
|---|---|---|
| 6,495,160 B2 | 12/2002 | Esposito et al. |
| 6,500,454 B1 | 12/2002 | Percel et al. |
| 6,500,457 B1 | 12/2002 | Midha et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 * | 12/2003 | Percel et al. .......... 424/457 |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 8,071,128 B2 | 12/2011 | Ohta et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Bruschi et al. |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |
| 2006/0121112 A1 | 6/2006 | Jenkins et al. |
| 2006/0233892 A1 | 10/2006 | Hendrix |
| 2006/0269607 A1 | 11/2006 | Percel et al. |
| 2007/0264358 A1 | 11/2007 | Wittlin |
| 2008/0069878 A1 | 3/2008 | Venkatesh et al. |
| 2009/0263480 A1 | 10/2009 | Lai et al. |
| 2011/0212171 A1 | 9/2011 | Venkatesh et al. |
| 2012/0135076 A1 | 5/2012 | Ohta et al. |

FOREIGN PATENT DOCUMENTS

| | | | |
|---|---|---|---|
| EP | 0239361 | | 9/1987 |
| EP | 0349103 | A1 | 1/1990 |
| EP | 0357369 | A2 | 3/1990 |
| EP | 0391518 | | 10/1990 |
| EP | 0431877 | | 6/1991 |
| EP | 0453001 | A1 | 10/1991 |
| EP | 0516345 | A1 | 12/1992 |
| EP | 0538034 | A1 | 4/1993 |
| EP | 0553777 | A2 | 8/1993 |
| EP | 0650826 | A1 | 5/1995 |
| EP | 0721777 | A2 | 7/1996 |
| EP | 0815931 | A1 | 1/1998 |
| EP | 0294493 | A1 | 12/1998 |
| EP | 0914818 | A1 | 5/1999 |
| EP | 0914823 | A1 | 5/1999 |
| EP | 1010423 | | 6/2000 |
| EP | 0582396 | B1 | 1/2001 |
| EP | 1070497 | A1 | 1/2001 |
| EP | 1072257 | A1 | 1/2001 |
| EP | 1157690 | A1 | 11/2001 |
| EP | 1156786 | B1 | 3/2003 |
| EP | 1366759 | A1 | 12/2003 |
| EP | 0914823 | B1 | 12/2004 |
| EP | 2319498 | A1 | 5/2011 |
| FR | 2679451 | A1 | 1/1993 |
| FR | 2766089 | A1 | 1/1999 |
| FR | 2778848 | | 11/1999 |
| FR | 2778848 | A1 * | 11/1999 |
| GB | 2053787 | A | 2/1981 |
| GB | 8824392.8 | | 9/1989 |
| GB | 2224207 | A | 5/1990 |
| JP | 41-11273 | B | 6/1966 |
| JP | 49-69819 | | 7/1974 |
| JP | 55-129224 | A | 10/1980 |
| JP | 56-014098 | A | 10/1981 |
| JP | 61-143316 | A | 7/1986 |
| JP | 62-61916 | A | 3/1987 |
| JP | 62-50445 | B2 | 10/1987 |
| JP | 62-242616 | A | 10/1987 |
| JP | 62-246513 | A | 10/1987 |
| JP | 62-252723 | A | 11/1987 |
| JP | 63-162619 | A | 7/1988 |
| JP | 63-270624 | A | 11/1988 |
| JP | 1-503385 | A | 11/1989 |
| JP | 1-313420 | A | 12/1989 |
| JP | 2-500747 | A | 3/1990 |
| JP | 2-164824 | A | 6/1990 |
| JP | 2-172918 | A | 7/1990 |
| JP | 2-289512 | A | 11/1990 |
| JP | 3-240724 | A | 10/1991 |
| JP | 4-224517 | A | 8/1992 |
| JP | 5-271054 | A | 10/1993 |
| JP | 5-310558 | A | 11/1993 |
| JP | 6-53658 | B2 | 7/1994 |
| JP | 6-321790 | A | 11/1994 |
| JP | 7-69889 | A | 3/1995 |
| JP | 7-124231 | A | 5/1995 |
| JP | 8-503482 | A | 4/1996 |
| JP | 8-175978 | A | 7/1996 |
| JP | 2002-154948 | A | 5/2002 |
| JP | 2003-522141 | A | 7/2003 |
| JP | 2005-508922 | A | 4/2005 |
| NZ | 550608 | A | 11/2005 |
| NZ | 554346 | A | 5/2006 |
| WO | WO 88/08703 | A1 | 11/1988 |
| WO | WO 88/08704 | A2 | 11/1988 |
| WO | WO 92/10173 | | 6/1992 |
| WO | WO 93/00097 | A1 | 1/1993 |
| WO | WO 93/12769 | A1 | 7/1993 |
| WO | WO 93/13758 | A1 | 7/1993 |
| WO | WO 93/15724 | A1 | 8/1993 |
| WO | WO 94/08576 | A1 | 4/1994 |
| WO | WO 94/12180 | A1 | 6/1994 |
| WO | WO 97/41878 | A1 | 11/1997 |
| WO | WO 97/47287 | A1 | 12/1997 |
| WO | WO 99/04763 | A1 | 2/1999 |
| WO | WO 9959557 | A1 * | 11/1999 |
| WO | WO 00/25752 | | 5/2000 |
| WO | WO 00/33821 | A1 | 6/2000 |
| WO | WO 00/42998 | | 7/2000 |
| WO | WO 00/51568 | A1 | 9/2000 |
| WO | WO 00/59486 | A2 | 10/2000 |
| WO | WO 01/13898 | | 3/2001 |
| WO | WO 01/72285 | A1 | 10/2001 |
| WO | WO 01/80829 | A2 | 11/2001 |
| WO | 02/13794 | | 2/2002 |
| WO | WO 02/43704 | A1 | 6/2002 |
| WO | WO 02/057475 | A1 | 7/2002 |
| WO | WO 02/085336 | A1 | 10/2002 |
| WO | WO 03/013492 | A1 | 2/2003 |
| WO | WO 03/039520 | A1 | 3/2003 |
| WO | WO 03/026613 | A1 | 4/2003 |
| WO | WO 03/041683 | A2 | 5/2003 |
| WO | WO 03/043661 | A1 | 5/2003 |

(56) References Cited

FOREIGN PATENT DOCUMENTS

| WO | WO 03/047552 A2 | 6/2003 |
|---|---|---|
| WO | WO 2004/009058 A1 | 1/2004 |
| WO | WO 2004/022037 A1 | 3/2004 |
| WO | WO 2004/087111 A1 | 10/2004 |
| WO | WO 2005/097064 A2 | 10/2005 |
| WO | WO 2005/105049 A2 | 11/2005 |

OTHER PUBLICATIONS

Ishino, R. et al., "Design and Preparation of Pulsatile Release Tablet as a New Oral Drug Delivery System," *Chem. Pharm. Bull.*, vol. 40, No. 11, pp. 3036-3041 (Nov. 1992).
Citation in the Third Party Observation in the Opposition of European Patent No. EP 0914818 B1.
Opposition Documents related to European Opposition of EP 0914818B1 (Opposition file history as of Mar. 9, 2009, excluding duplicative, purely administrative documents (97 pages total)).
Villa, "European Search Report," 5 pages, from European Patent Appl. No. 11171982.9, European Patent Office, Munich, Germany (mailed Dec. 22, 2011).
Young, "International Search Report," 2 pages, PCT appl. No. PCT/US11/20493, United States Patent and Trademark Office (mailed Mar. 23, 2011).
Young, "Written Opinion of the International Searching Authority," 6 pages, PCT appl. No. PCT/US11/20493, United States Patent and Trademark Office (mailed Mar. 23, 2011).
"Low Substituted Hydroxypropylcellulose," Official Monographs for Part II, 2001, NRF, JP XIV, pp. 942-943.
Albrecht, "International Search Report," 6 pages, from International Patent Appl. No. PCT/US02/31535, European Patent Office (Feb. 3, 2003).
Anwar et al., "Chronotherapeutics for Cardiovascular Disease," Drugs 55(5):631-643 (1998).
Bauer et al., Pharmarzeutische Technologie, 5$^{th}$ Edition, 1997, Govi Verlag Frankfurt, pp. 164-166.
Berigan, "Atomoxetine Used Adjunctively With Selective Serotonin Reuptake Inhibitors to Treat Depression," Prim. Care. Companion J. Clin. Psychiatry 6(2):93-94 (2004).
Bodmeier et al., "Theophylline Tablets Coated with Aqueous Latexes Containing Dispersed Pore Formers," J. Pharm. Sci. 79(10):925-928 (1990).
Database WPI, Section Ch, Week 198748, Derwent Publications, Ltd., London, GB; AN 1987-338131, XP002156870.
Fell, Letter to the Editor, J. Pharm. Pharmacol. 1968, vol. 20, pp. 657-658.
FMC Corporation Product Specification for Avicel PH, 2005.
Foreign non-patent publication from Japanese textbook, 1989, Hirokawa Publishing Co.
Foreign non-patent publication Sysmex No. FP30SCJ001, 2007.
Fubara, "International Preliminary Examination Report," 3 pages, from International Patent Appl. No. PCT/US02/31535, European Patent Office (Jun. 19, 2003).
Gordon et al., "Effect of the Mode of Super Disintegrant Incorproration on Dissolution in Wet Granulated Tables," J. Pharm. Sci. 82:220-226 (1993).
Gorman et al., An Evaluation of Croscarmellose as a Tablet Disintegrant in Direct Compression Systems, Drug. Dev. Ind. Pharm. 1982; vol. 8, pp. 397-410.
Handbook (Binran) of Granule, vol. 1, Ohmsha Ltd., p. 434 & 438 (May 3, 1975).
Kaneto et al., 2000, Latest Pharmacy, Hirokawa Publishing Co., 1 Edition.
Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Exp. Opin. Pharmacother. 4(7):1165-1174 (2003).
McKenna et al., "Effect of particle size on the compaction mechanism and tensile strength of tablets," J. Pharm. Pharmacol. Jun. 1982, vol. 34(6), pp. 347-351.
McKetta et al., "Table of Contents," Encyclopedia of Chemical Processing and Design (1989).
McKetta et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd.
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Oh, "International Preliminary Report on Patentability," 5 pages, from International Appl. No. PCT/US2005/037084, United States Patent and Trademark Office, Alexandria, Virginia, USA (mailed Aug. 24, 2007).
Ohira et al., "Effects of Various Histamine $H_2$-Receptor Antagonists on Gastrointestinal Motility and Gastric Emptying," J. Smooth Muscle Res. 29:131-142 (1993).
Pharmaceutical Excipients. London: Pharmaceutical Press. Electronic Version, 2006, Mannitol.
Pharmaceutical Excipients. London: Pharmaceutical Press. Electronic Version, 2006, Lactose Monohydrate.
Pharmaceutical Excipients. London: Pharmaceutical Press. Electronic Version, 2006, Croscarmellose sodium.
Rankin, "International Search Report," 6 pages, PCT International Application No. PCT/US02/39238, European Patent Office (May 8, 2003).
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).
Schifferer, "International Search Report," 4 pages, from International Appl. No. PCT/US2005/037084, European Patent Office, Rijswijk, The Netherlands (mailed Jun. 1, 2006).
Schifferer, "Written Opinion of the International Search Authority," 6 pages, from International Appl. No. PCT/US2005/037084, European Patent Office, Munich, Germany (mailed Jun. 1, 2006).
Shangraw et al., "A new era of tablet disintegrants," Pharm. Technol. 1980, vol. 4(10), pp. 49-57.
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, "International Search Report," 5 pages, International Patent Appl. No. PCT/US2006/016538, European Patent Office (Feb. 27, 2007).
Uhl, "Written Opinion of the International Searching Authority," 6 pages, International Patent Appl. No. PCT/US2006/016538, European Patent Office (Feb. 27, 2007).
van Kamp et al., "Improvement by super disintegrants of the properties of tablets containing lactose, prepared by wet granulation," Pharmaceutisch Weekblad Scientific Edition; 1983, vol. 5, pp. 165-171.

(56) References Cited

OTHER PUBLICATIONS

Villa, "International Search Report," 4 pages, from International Appl. No. PCT/US2005/038328, European Patent Office, Rijswijk, The Netherlands (mailed Sep. 15, 2006).

Villa, "Written Opinion of the International Search Authority," 5 pages, from International Appl. No. PCT/US2005/038328, European Patent Office, Munich, Germany (mailed Sep. 15, 2006).

Vromans et al., "Studies on tableting properties of lactose," Pharmaceutisch Weekblad Scientific Edition; 1985, vol. 7, pp. 186-193.

Yamahara et al., "Effect of release rate on bioavailability of control-release multiple unit dosage forms," Yakuzaigaku 55(2):99-107 (1995).

Yamamoto et al., "The Effects of Nizatidine on the Function of Esophageal Motility in Patients with Gastroesophageal Reflux Disease (GERD)," Jpn. Pharmacol, Ther. 28(5):419-424 (2000).

Young, "International Preliminary Examination Report" 6 pages, PCT International Application No. PCT/US02/39238, United States Patent and Trademark Office (Apr. 27, 2005).

Young, "Written Opinion," 5 pages, PCT International Application No. PCT/US02/39238, United States Patent and Trademark Office (Jan. 13, 2005).

Zimmer, "European Search Report," 3 pages, European patent appl. No. 01103129.1, European Patent Office (Jun. 9, 2001).

Zimmer, "International Search Report," 4 pages, PCT International Application No. PCT/US01/04012, European Patent Office (Jun. 19, 2001).

* cited by examiner

TIMED, PULSATILE RELEASE SYSTEMS

TECHNICAL FIELD

The present invention relates to the development of timed, pulsatile release bead populations comprising one or more alkaline pharmaceutical actives exhibiting release of the drug after a predetermined delay (lag time) of more than about 5 hours and to the production of oral drug delivery systems to target PK (pharmacokinetics, i.e., plasma concentration-time) profiles suitable for a twice- or once-daily dosing regimen, thereby minimizing potential risks of adverse side effects, enhancing patient compliance and therapeutic efficacy, and reducing cost of treatment.

BACKGROUND OF THE INVENTION

Many therapeutic agents are most effective when made available at constant rates at or near the absorption sites. The absorption of therapeutic agents thus made available generally results in desired plasma concentrations leading to maximum efficacy, and minimum toxic side effects. Much effort has been devoted to developing sophisticated drug delivery systems such as osmotic devices for oral application. However, there are instances where maintaining a constant blood level of a drug is not desirable. For example, a major objective of chronotherapy for cardiovascular diseases is to deliver the drug in higher concentrations during the time of greatest need, e.g., the early morning hours, and in lesser concentrations when the need is less, e.g., during the late evening and early sleep hours. In addition to a properly designed drug delivery system, the time of administration is equally important. The unique pharmacokinetic profile needed can be calculated from a simulated modeling developed using the pharmacokinetic parameters, knowledge of drug solubility, absorption along the gastrointestinal tract and elimination half-life.

A timed, pulsatile delivery system capable of providing one or more immediate release pulses at predetermined lag times or at specific sites result in better absorption of the active and more effective plasma profile. However, there are only a few such orally applicable pulsatile release systems due to potential limitations of the dosage form size, and/or polymeric materials and their compositions used for producing dosage forms. Ishino et al. disclose a dry-coated tablet form in Chemical Pharm. Bull. Vol. 40 (11), p 3036-3041 (1992). U.S. Pat. No. 4,871,549 assigned to Fujisawa Pharmaceutical Company discloses the preparation of a time-controlled explosion system in which rapid-release pulses at predetermined time intervals are caused by explosion of the membrane surrounding the drug cores comprising swelling agents such as disintegrants (e.g., low-substituted hydroxypropylcellulose, crospovidone, crosslinked carboxymethylcellulose, sodium starch glycolate). These systems are rather difficult to manufacture and do not consistently perform.

U.S. Pat. No. 6,531,152 discloses an explosion-controlled drug delivery system comprising a core containing a drug in combination with a core material (such as a polysaccharide or a crosslinked protein and a disintegrant that swell on exposure to body fluids or water) having a rigid membrane comprising hydrophobic and hydrophilic polymers that bursts rapidly releasing the active when the core swells. The '152 patent discloses specific tablet formulations having lag-times of up to about 12 hours. U.S. Pat. No. 6,287,599 to Burnside et al. discloses a pharmaceutical composition (a tablet formulation) comprising at least one pharmaceutically active agent that has a pH dependent solubility, at least one non-pH dependent sustained release agent and at least one pH-dependent agent that increases the dissolution rate of the active at a pH in excess of 5.5. Such a system exhibits approximately pH independent drug release profile.

However, monolithic drug delivery systems exhibit variable gastrointestinal transit times, and multiparticulate dosage forms containing coated drug particles (beads, pellets or micro-tablets) exhibiting consistent GI transit times are preferred.

The pulsatile burst release times in the above-described delivery systems are controlled by choosing appropriate core material, and by varying the membrane composition and/or thickness. However, it is difficult to consistently manufacture quality products based on such drug delivery systems wherein the drug-release is controlled by a swelling agent, a hydrophobic excipient, an osmotic agent alone or mixtures thereof.

U.S. Pat. No. 6,627,223, assigned to Eurand Pharmaceutical Limited, which is incorporated herein by reference, discloses a pulsatile release system consisting of a combination of one or more bead populations, each with a well-defined release profile. A timed, sustained-release profile (i.e., a sustained-release profile over a 12 to 24 hours after a lag-time of about 4 hours (i.e., a period of little or no release) following oral administration is disclosed in U.S. Pat. No. 6,500,454, and a biphasic release profile (i.e., an immediate-release pulse and a rapid burst after a lag-time of about 3 hours) is disclosed in U.S. Pat. No. 6,663,888. Although, a lag-time of greater than 3 hours could be achieved by applying a membrane comprising a water-insoluble polymer such as ethylcellulose (Ethocel Standard Premium 10 cps available from Dow Chemical Company) and an enteric polymer such as hydroxypropyl methylcellulose phthalate (HP-55 available from Shin-Etsu Chemical Corporation, Tokyo, Japan) on drug-layered beads containing propranolol hydrochloride (56% drug-load coated on 25-30 mesh sugar spheres) at 10-15% weight gain, the same coating composition applied on drug-layered beads containing nizatidine (56% drug-load coated on 25-30 mesh sugar spheres) even at 35-39% by weight resulted in a lag-time of less than 3 hours. It was considered in the prior art that the solubility of therapeutic agent in the dissolution medium and/or the molecular weight of the agent determined the drug dissolution within the coated bead and its diffusion out of the membrane. After extensive investigations, it was surprisingly discovered that apart from pH-dependent solubility of the therapeutic agent, its acidity/alkalinity has a significant effect on the lag-time that could be achieved. Additionally, the impact of a barrier coating (i.e., an intermediate coating applied in between the inner protective seal coat and the outer lag time coating, hereafter referred to as the barrier coat) and/or its composition on lag-time that could be achieved can vary depending on the acidity/alkalinity of the actives.

SUMMARY OF THE INVENTION

The present invention provides a pulsatile delivery system suitable for a twice-daily or once-daily dosing regimen by oral administration of a specific therapeutic agent depending on its acidity/alkalinity, solubility in gastrointestinal fluids, and its elimination half-life. The pulsatile delivery system comprises one or more bead populations, such as immediate release (IR) Beads and timed, pulsatile-release (TPR) bead populations. Each TPR bead population releases the drug as a rapid burst or as a sustained-release profile after a pre-determined lag-time (for example, 10 hours or longer is achievable) upon oral administration. The IR Beads may be simply drug cores coated with a protective membrane (for example, a coating with Opadry Clear). These IR Beads with a barrier coating are coated with a functional membrane of a mixture of water insoluble and enteric polymers, a plasticized polymeric system being applied from aqueous or solvent based composition. The finished dosage form may be a modified-release (MR) capsule, a standard (conventional) tablet or an orally disintegrating tablet (ODT) comprising a coated spherical bead population containing the active substance alone or a combination of two or more coated bead populations to provide target plasma concentrations suitable for a once or twice-daily dosing regimen. For example, a once-daily dosage form of an active with an elimination half-life of about 7 hours may contain a mixture of an IR bead population which allows immediate release, a second, TPR bead population with a shorter lag-time (about 3-4 hours), which allows a delayed "burst" release and a third, TPR bead population with a longer lag-time (about 6-9 hours), which allows a delayed, typically sustained-release profile of an active with an elimination half-life of about 7 hours, thus enhancing safety, therapeutic efficacy and patient compliance while reducing cost of treatment. The achievable lag time depends on the composition and thickness of the barrier coating, the composition and thickness of the lag-time coating, as well as the nature of the therapeutic agent. Specific factors that can affect the lag-time include, but are not limited to, the therapeutic agent's alkalinity/acidity, solubility, elimination half-life, and dosing (twice-daily or once-daily) regimen.

BRIEF DESCRIPTION OF THE FIGURES

The invention will be described in further detail with reference to the accompanying Figures wherein.

DETAILED DESCRIPTION OF THE INVENTION

Figure 1:
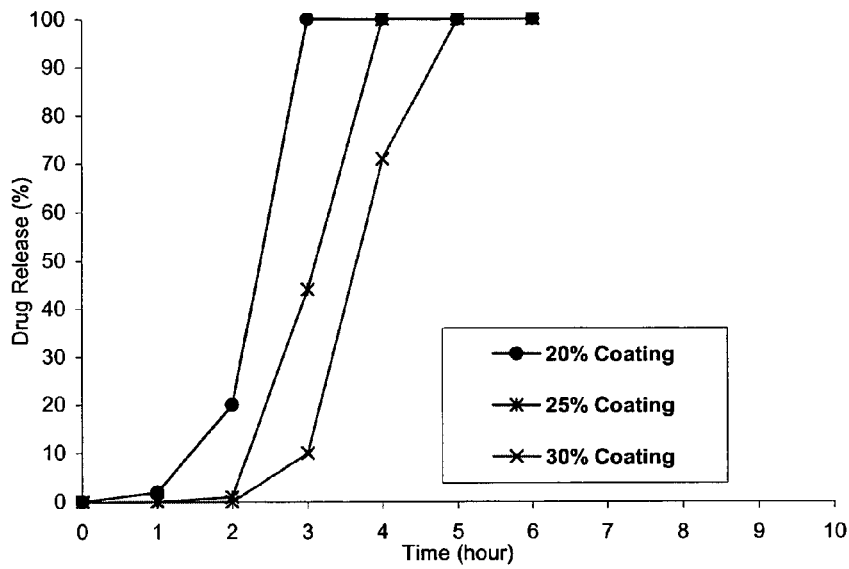
FIG. 1 shows drug release profiles of nizatidine IR beads (without a barrier coating) coated with EC/HPMCP at 20, 25 and 30% by weight of Example 1C.

Active pharmaceutical ingredients (API) typically are either slightly acidic or basic when suspended in purified water (see Table 1). The extent of acidity or alkalinity varies significantly. For example, the pH can range from as low as 5.7-6.5 for propranolol hydrochloride to a pH of 6.5-8.7 for nizatidine to as high as a pH of 7.9-11.0 for atenolol. An active pharmaceutical ingredient exhibiting a pH of 7.0, or less, when suspended in water at a solid content of 2 g/mL is designated as an acidic drug in this invention disclosure while an API exhibiting a pH of 7.0, or greater, is designated as an alkaline drug.

TABLE 1

| pH of representative drugs suspended in water | | | | |
| --- | --- | --- | --- | --- |
| Drug | Acidity/Alkalinity | PH of Solution/Suspension | | |
| Drug Concentration (solid content) | | 0.2 g/mL | 2.0 g/mL | 20 g/mL |
| Propranolol Hydrochloride | Acidic | pH = 5.7 | pH = 6.0 | pH = 6.5 |
| Nizatidine | Alkaline | pH = 6.5 | pH = 7.4 | pH = 8.7 |
| Drug concentration (solid content) | | 0.1 g/mL | 1.0 g/mL | 10 g/mL |
| Cyclobenzaprine Hydrochloride | Acidic | pH = 6.1 | pH = 6.5 | pH = 6.7 |
| Atenolol | Alkaline | pH = 7.9 | pH = 10.9 | pH = 11.0 |

Since the polymer blend system typically utilized to delay the onset of drug-release by several hours upon oral administration is a mixture of water-insoluble and enteric polymers, the extent of delayed onset depends on the acidity/alkalinity of the API. The present invention provides a method for manufacturing a pharmaceutically elegant multi-particulate dosage form having timed, pulsatile release profiles, i.e., a well time-controlled single pulse or a series of pulses occurring several hours after oral administration. The present invention also provides a multicoated, multiparticulate dosage form having an active core, an intermediate barrier-coating and an outer membrane of a mixture of water-insoluble polymer and an enteric polymer. A barrier coating applied on IR beads may comprise an enteric polymer, a water-insoluble polymer or a mixture of water-insoluble and water-soluble polymers. The polymers used in forming the barrier coating and the outer membrane may be plasticized.

In accordance with one aspect of the present invention, the active core of the dosage form may comprise an inert particle, which is coated with a drug-containing film-forming formulation and, in accordance with certain embodiments, an inert particle is coated with a water-soluble film forming composition to form a water-soluble/dispersible particle. The amount of drug in the core will depend on the drug and the dose that is desired. Generally, the core in accordance with this aspect of the invention will contain about 5 to 60% by weight of the drug based on the total weight of the core. Those skilled in the art will be able to select an appropriate amount of drug for coating or incorporation into the core to achieve the desired dosage form.

The active core of the dosage form of certain embodiments of the present invention may comprise an inert particle such as a sugar sphere with a desired mean particle size. In one embodiment, the inactive core may be a sugar sphere, a cellulose sphere, a spheroidal silicon dioxide bead, a buffer crystal or an encapsulated buffer crystal, such as calcium carbonate, sodium bicarbonate, fumaric acid, tartaric acid, etc. Buffer crystals are useful to alter the microenvironment. Alternatively in accordance with other embodiments, drug-containing microgranules or pellets may be prepared by rotogranulation, high-shear granulation and extrusion-spheronization or compression (as mini-/micro-tablets (about one/two mm in diameter)) of the drug, a polymeric binder and optionally fillers/diluents.

Active cores comprising an inert particle coated with a drug-containing film forming binder can be prepared in accordance with the following process. An aqueous or a pharmaceutically acceptable solvent medium may be used for preparing core particles based on coated inert particles. The type of inert binder that is used to bind the water-soluble drug to the inert particle is not critical but usually water soluble or alcohol soluble binders, such as polyvinylpyrrolidone (PVP or povidone) or hydroxypropylcellulose may be used. The binder may be used at any concentration capable of being applied to the inert particle. Typically, the binder is used at a concentration of about 0.5 to 10% by weight. The drug substance may be present in this coating formulation in solution form or may be suspended. The drug concentration may vary depending on the application but typically will be used at concentrations from about 10 to 30% by weight depending on the viscosity of the coating formulation.

In accordance with other embodiments, the active core may be prepared by rotogranulation, or by granulation followed by extrusion-spheronization or tableting into micro/mini-tablets. The drug substance, a binder, an optional dissolution rate controlling polymer, and optionally other pharmaceutically acceptable excipients (e.g., diluents/fillers) may be blended together in a high-shear granulator, such as Fielder granulator, or a fluid bed granulator, such as Glatt GPCG granulator, and granulated to form agglomerates by adding/spraying a granulating fluid such as water or alcohol and dried. The wet mass can be extruded and spheronized to produce spherical particles (pellets) using an extruder/marumerizer. The blend comprising drug particles, a binder and optionally a filler/diluent or drug-containing granules can also be compressed into mini-tablets (about 2 mm in diameter) or micro-tablets (about 1 mm in diameter) to produce IR pellets. In these embodiments, the drug load could be as high as 95% by weight based on the total weight of the extruded or granulated core.

Generally, the individual polymeric coatings on the active core will vary from about 1.5 to 60% by weight depending on the nature of the active, composition of the barrier coat, and required lag-time. In one embodiment, the core with a high drug-load may be provided with a barrier-coat of a plasticized water-insoluble polymer, such as ethylcellulose (EC), at about 1.5-15% by weight to sustain the drug-release over about 5-20 hours. In certain other embodiments, the core with a high drug-load may be provided with a barrier-coat of a plasticized enteric polymer, such as hydroxypropyl methylcellulose phthalate (HPMCP), at about 5-20% by weight. In yet another embodiment of the present invention, the active core may be provided with an outer lag-time coating of EC/HPMCP/plasticizer at about 45.5/40/14.5 for a weight gain of about 30-60% by weight to lengthen the lag-time up to about 10 hours or longer.

Both the barrier and outer (hereafter referred to as lag-time) membrane coatings on water-soluble/dispersible drug containing particles (IR beads) may comprise a plasticizer. The intermediate or barrier membrane may comprise an enteric polymer such as hydroxypropyl methylcellulose phthalate (HPMCP) or a water-insoluble polymer (e.g., ethylcellulose) alone or in combination with one or more water-soluble/pore-forming polymer such as HPMC, methyl cellulose, hydroxypropyl cellulose (HPC), polyethylene glycol (PEG) or polyvinylpyrrolidone (PVP). When the barrier coating comprises a water-insoluble polymer in combination with a water-soluble/pore-forming polymer, the polymers are typically present at a ratio from about 9:1 to 5:5, water-insoluble polymer to water-soluble polymer. The barrier coating is typically applied for a weight gain of from about 1.5 to 15% by weight.

The outer lag-time membrane may comprise a plasticized mixture of a water-insoluble polymer and an enteric polymer wherein the water-insoluble polymer and the enteric polymer may be present at a weight ratio of about 10:1 to 1:2 and typically about 3:1 to 1:1. The total weight of the lag coating varies from about 30 to 60% and more particularly from about 40 to 55% by weight based on the weight of the coated bead.

Cores comprising a slightly basic drug, such as nizatidine, may be provided with only the lag-time coating (no barrier coating) of EC/HPMCP/plasticizer at about 45.5/40/14.5 for a weight gain of about 40% by weight, which may result in a lag-time of about 3 hours or less. In contrast, cores comprising a slightly acidic drug, such as propranolol hydrochloride, may be provided with only the lag-time coating of EC/HPMCP/plasticizer at about 45.5/40/14.5 for a weight gain of about 40% by weight, which could result in a lag-time of about 6 hours or longer. Those skilled in the art will be able to select an appropriate amount of active for coating onto or incorporating into the core to achieve the desired dosage.

In accordance with one particular embodiment of the present invention, the water soluble/dispersible drug-containing particle is coated with a mixture of a water insoluble polymer and an enteric polymer. The water insoluble polymer and enteric polymer may be present at a weight ratio of from about 10:1 to 1:2, more particularly from about 2:1 to 1:1, and the total weight of the coatings is about 30 to 60% by weight based on the total weight of the coated beads. The polymeric coatings typically contain plasticizers and may be applied from aqueous and/or solvent-based systems.

The composition of the membrane layer and the individual weights of the polymers are important factors to be considered for achieving a desired lag time prior to appreciable drug release. The coated beads may optionally have a barrier layer of pharmaceutical glaze (shellac) under the lag-time coating, which basically dictates the lag time.

The invention also provides a method of making timed, pulsatile release beads comprising the steps of:
1. preparing drug-containing cores by coating inert particles, such as sugar spheres or cellulose spheres, with one or more active pharmaceutical ingredients from a polymeric binder solution/suspension and applying a protective seal-coat to form immediate release (IR) beads;
2. coating the IR beads with a plasticized a) water-insoluble polymer alone or in combination with a water-soluble polymer or b) enteric polymer to form barrier-coated beads with a membrane thickness of from about 1.5% to 20% by weight;
3. coating the barrier-coated beads with a plasticized mixture of a water-insoluble polymer and an enteric polymer with a membrane thickness of from about 40% to 60% by weight to form TPR (Timed Pulsatile Release) beads exhibiting a lag-time of up to about 10 hours or longer; and
4. filling two or more bead populations—IR beads and one or more TPR bead populations, wherein each TPR bead population may exhibit different lag-times into hard gelatin capsules, or compressing into conventional tablets or orally disintegrating tablets, to produce a once-daily or twice-daily capsule formulation.

The release profiles for IR, barrier-coated and TPR beads may be determined according to the following procedure:

Dissolution testing of IR beads and enteric coated beads (for acid resistance testing) is conducted with a USP Apparatus 1 (baskets at 100 rpm) or Apparatus 2 (paddles at 50 rpm) in 900 mL of 0.1N HCl at 37° C. while the dissolution testing of TPR beads is conducted in a USP apparatus using a two-stage dissolution medium (first 2 hours in 700 mL of 0.1N HCl at 37° C. followed by dissolution testing at pH=6.8 obtained by the addition of 200 mL of pH modifier). Drug release with time is determined by HPLC on samples pulled at selected intervals.

The TPR Beads prepared in accordance with present invention may be designed to provide a target drug-release profile, such as a rapid pulse or a sustained-release profile following a pre-determined lag-time. Even in the absence of the barrier coating, thicker lag-time coatings typically provide moderately sustained rather than rapid pulses (see FIG. 3 for details). The multiparticulate dosage form may be provided as a single TPR bead population alone or a TPR bead population combined with an IR bead population and/or one or more additional TPR bead populations providing different release profiles. In accordance with one embodiment, a multiparticulate dosage form is provided with at least an IR bead population, a first TPR population and a second TPR population wherein the ratio of IR bead to the first and second TPR bead population varies from about 10/20/70 to about 30/60/10, respectively, depending on factors such as alkalinity, pH-dependent solubility, and/or elimination half-life of the active ingredient.

There are instances wherein the onset of drug release should begin several hours following oral administration to provide adequate plasma concentration to be suitable for a once-daily dosing regimen, depending on the elimination half-life of the active. In accordance with particular aspects of the invention, drug release may be delayed for up to about 10-15 hours after oral administration.

A single targeted sustained-release profile over several hours after oral administration, with or without an immediate release pulse, is provided in accordance with certain of the timed pulsatile release drug delivery systems of the present invention.

In accordance with one aspect of the invention, one or more active ingredients, a binder such as hydroxypropylcellulose (Klucel LF), a dissolution rate controlling polymer (if used), and optionally other pharmaceutically acceptable excipients are blended together in a high shear granulator such as Fielder or a fluid bed granulator such as Glatt GPCG 5 and granulated to form agglomerates by adding/spraying a granulating fluid such as water or alcohol and dried. The wet mass can be extruded and spheronized to produce spherical particles (beads) using an extruder/marumerizer. In accordance with another embodiment of the invention, dried granules may be compressed into pellets (i.e., mini or micro-tablets) with a diameter of about 1 mm to 2 mm. In these embodiments, the drug load could be as high as 95% by weight based on the total weight of the extruded/spheronized or mini-/micro-tablet core.

In accordance with a specific embodiment, the active containing cores (beads, pellets, mini-/micro-tablets or granular particles) thus obtained are coated with a lag-time coating comprising a water-insoluble polymer and an enteric polymer, such as ethylcellulose and hypromellose phthalate (i.e., hydroxypropyl methylcellulose phthalate or HPMCP) at a thickness from about 10 to 60%, more particularly from about 30% to 60%, by weight based on the total weight of the coated beads. The ratio of water insoluble polymer to enteric polymer may vary from about 10:1 to 1:2, more particularly from about 2:1 to 1:1.

An aqueous or a pharmaceutically acceptable solvent medium may be used for preparing core particles. The type of inert binder that is used to bind the water-soluble drug to the inert particle is not critical but usually water-soluble or alcohol soluble binders are used. Representative examples of binders include, but are not limited to, polyvinylpyrrolidone (PVP), hydroxypropyl methylcellulose (HPMC), hydroxypropylcellulose, carboxyalkylcelluloses, polyethylene oxide, polysaccharides such as dextran, corn starch, which may be dissolved or dispersed in water, alcohol, acetone or mixtures thereof. The binders are typically used at a concentration of from about 0.5 to 10% by weight.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of water-insoluble polymers useful in the invention include ethylcellulose, polyvinyl acetate (for example, Kollicoat SR#30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Dissolution rate controlling polymers suitable for incorporating in the formulation for producing granules by high shear or fluid bed granulation or by dry granulation include high molecular weight hydroxypropyl methylcellulose, hydroxypropyl cellulose, ethyl cellulose, sodium carboxymethyl cellulose, alginic acid, polymethylmethacrylate copolymers and polyvinyl acetate/crotonic acid copolymer or combinations thereof.

Both enteric and water-insoluble polymers used in forming the membranes are usually plasticized. Representative examples of plasticizers that may be used to plasticize the membranes include triacetin, tributyl citrate, triethyl citrate, acetyl tri-n-butyl citrate, diethyl phthalate, castor oil, dibutyl sebacate, acetylated monoglycerides, acetylated diglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

In general, it is desirable to prime the surface of the particle before applying the membrane coatings or to separate the different membrane layers by applying a thin hydroxypropyl methylcellulose (HPMC) (Opadry Clear) film. While HPMC is typically used, other primers such as hydroxypropylcellulose (HPC) can also be used.

The active pharmaceutical ingredients suitable for incorporation into these time-controlled pulsatile release systems include basic bioactive molecules or their salts. The drug substance can be selected from the group of pharmaceutically acceptable chemical entities with proven pharmacological activity in humans. Reprentative examples include analgesics, anticonvulsants, antidiabetic agents, anti-infective agents, antineoplastics, antiparkinsonian agents, antirheumatic stimulants, cardio vascular agents, CNS (central nervous system) stimulants, dopamine receptor agonists, gastrointestinal agents, psychetherapeutic agents, opioid agonists, opioid antagonists, urinary tract agents, antiemetics, anti-epileptic drugs, histamine $H_2$ antagonists, skeletal muscle relaxants, and antiasthmatic agents.

The membrane coatings can be applied to the core using any of the coating techniques commonly used in the pharmaceutical industry, but fluid bed coating is particularly useful. The present invention is directed to multi-dose forms, i.e., drug products in the form of multi-particulate dosage forms (hard gelatin capsules, conventional tablets or ODTs (orally disintegrating tablets)) comprising one or more bead populations for oral administration to provide target PK profiles in patients in need of treatment. The conventional tablets rapidly disperse on entry into the stomach while ODTs rapidly disintegrate in the oral cavity forming a suspension of coated beads for easy swallowing. One or more coated bead populations may be compressed together with appropriate excipients into tablets (for example, a binder, a diluent/filler, and a disintegrant for conventional tablets while a rapidly dispersing granulation may replace the binder-diluent/filler combination in ODTs).

The following non-limiting examples illustrate the capsule dosage forms comprising one or more pulses, each with a predetermined delayed-onset and the totality of the in vitro drug-release profile or the ensuing in vivo plasma concentration profile upon oral administration of the dosage form should mimic the desired profile to achieve maximum therapeutic efficacy to enhance patient compliance and quality of life. Such dosage forms, when administered at the 'right time', would enable maintaining drug plasma concentration at a level potentially beneficial in minimizing the occurrence of side-effects associated with $C_{max}$ or $C_{min}$.

Example 1

Inventive

A. IR Beads of Nizatidine

Nizatidine (168 kg) was slowly added to an aqueous solution of hydroxypropylcellulose such as Klucel LF (18.6 kg) and mixed well. #25-30 mesh sugar spheres (107.4 kg) were coated with the drug suspension in a Glatt fluid bed coater, equipped with a 32" bottom spray Wurster insert. The drug containing particles were dried, and a seal coat of Opadry Clear (2% w/w) was first applied and dried in the Glatt fluid bed unit as a precautionary measure to drive off excessive surface moisture. The drug load was 56% w/w.

B. Nizatidine Beads with a Barrier-Coating of HPMCP:

IR beads produced above were coated in Glatt GPCG 5 equipped with a bottom spray Wurster insert with HPMCP (e.g., hypromellose phthalate, HP-55 commercially available from Shin Etsu) and triethyl citrate (TEC) as a plasticizer at a ratio of 90/10 dissolved in 98/2 acetone/water for a weight gain of 10% based on the weight of the coated beads.

C. Nizatidine TPR Beads without a Barrier-Coating of HPMCP:

Drug containing IR Beads from Step A above were provided with an outer membrane by spraying a solution of 45.5/40/14.5 EC/HPMCP/TEC (ethylcellulose/HPMCP/triethylcitrate) in 98/2 acetone/water in a fluid bed coater for a weight gain of approximately 20%, 25% and 30%. The coated particles were unit cured at 60° C. for 10 minutes to produce TPR Beads (batch size: 4 kg).

D. Nizatidine TPR Beads with a Barrier-Coating of HPMCP:

The enteric-coated beads from Step B above were provided with an outer membrane by spraying a solution of 45.5/40/14.5 EC/HPMCP/TEC in 98/2 acetone/water in a fluid bed coater for a weight gain of approximately 20%, 30%, and 40%. The coated particles were unit cured at 60° C. for 10 minutes to produce TPR Beads (batch size: 4 kg).

E. Nizatidine TPR Beads with a Barrier-Coating of EC/HPC:

IR beads produced above (Step A) were coated in Glatt GPCG 5 equipped with a bottom spray Wurster insert with ethylcellulose and hydroxypropylcelluse (e.g., Klucel LF commercially available from Aqualon) at a ratio of 70/30 dissolved in acetone/water plasticized with TEC for a weight gain of 5% based on the weight of the coated beads. These barrier-coated beads were provided with an outer membrane by spraying a solution of 45.5/40/14.5 EC/HPMCP/TEC in 98/2 acetone/water in a fluid bed coater for a weight gain of approximately 20%, 30% and 40%. The coated particles were unit cured at 60° C. for 10 minutes to produce TPR Beads (batch size: 4 kg).

Example 2

Comparative

A. IR Beads of Propranolol HCl:

Propranolol HCl (168 kg) was slowly added to an aqueous solution of polyvinylpyrrolidone (8.8 kg Povidone K-30) and mixed well. 25-30 mesh sugar spheres (117.2 kg) were coated with the drug solution in a Glatt fluid bed granulator equipped with 32" bottom spray Wurster insert. The drug containing pellets were dried, and a seal coat of Opadry Clear (6.0 kg) was first applied and dried in the Glatt fluid-bed unit as a precautionary measure to drive off excessive surface moisture. The drug load was 56% w/w.

B. Propranolol HCl Beads with a Barrie-Coating of HPMCP:

IR beads produced above were coated in Glatt GPCG 5 equipped with a bottom spray Wurster insert with HPMCP and TEC at a ratio of 90/10 dissolved in 98/2 acetone/water for a weight gain of 10% based on the weight of the coated beads.

C. Propranolol HCl TPR Beads (without Barrier-Coating):

IR beads produced in Step A above were coated in Glatt GPCG 5 with ethylcellulose, HPMCP and triethyl citrate at a ratio of 45.5/40/14.5 dissolved in 98/2 acetone/water for a weight gain of 20%, 30% and 40% based on the weight of the coated beads.

D. Propranolol HCl TPR Beads (with a Barrier-Coat of EC):

IR beads produced in Step A above were coated in fluid-bed equipment (Fluid Air FA0300 equipped with a 32" bottom spray Wurster insert) with ethylcellulose and diethyl phthalate (DEP) as a plasticizer at a ratio of 90/10 for a weight gain of 1.8% by weight. This coating was followed by a lag-time coating of EC/HPMCP/DEP at a ratio of 45.5/40/14.5 dissolved in 98/2 acetone/water for a weight gain of 15%, based on the weight of the coated beads.

Drug Release Testing: The drug release profiles were generated by dissolution testing per US Pharmacopoeia method (Apparatus 1 with baskets at 100 rpm or Apparatus 2 with paddles at 50 rpm) using 700 mL of pH 1.2 buffer for 2 hours followed by testing in 900 mL of pH 6.8 for the remaining time-points). The IR and enteric-coated beads were tested in 900 mL of 0.1N HCl for 1 and 1.5 hrs, respectively. The samples pulled at different time-points were quantified by HPLC.

Example 3

Stability of Coated Beads

Nizatidine TPR beads of Example 1D coated with EC/HPMCP at 40% were packaged in induction-sealed HDPE bottles, placed on stability at 40° C./75% RH and samples were pulled at 1, 2, 3 and 6-month time points. Dissolution tests were performed using the procedures detailed above. The TPR beads stored at accelerated stability conditions exhibited acceptable stability for at least 6 months.

Drug Release Profile:

Finished capsules may comprise one or more TPR bead populations with desired lag-times or in combination with IR beads at a desired ratio and in sufficient quantities to provide target in vitro drug-release profiles and hence target pharmacokinetics (PK) profiles suitable for a twice-daily or once-daily dosing regimen. When tested under in vitro conditions following the dissolution test procedure listed above, the IR beads which are designed to provide a loading dose typically release substantially all of the drug within the first hour, preferably within the first 30 minutes. The Timed Pulsatile Release (TPR) Beads are designed to begin releasing the drug after a lag-time of up to several hours (a period of minimal drug-release (less than about 10% of the dose) following oral administration). The pulse may be a rapid burst or spread over a period ranging from about 2 hours to about 20 hours depending on the thickness of the lag-time coating and/or the barrier-coat.

Acid-Resistance of Nizatidine and Propranolol Beads Coated with HPMCP

The enteric polymer coating applied on nizatidine IR beads of Example 1B more or less disintegrated within an hour releasing most of the dose in the acidic buffer although the enteric polymer was not supposed to dissolve. In contrast, the enteric-coated beads of propranolol hydrochloride of Example 2B exhibited the expected acid-resistant property by releasing not more than 1% of the dose in 1.5 hours of dissolution testing at pH 1.2. Although not wishing to be bound by theory, it appears the water imbibed into the core of coated nizatidine beads dissolves some nizatidine creating an alkaline pH environment, which tends to destroy the enteric polymer membrane on the enteric coated IR beads, even though the dissolution medium is acidic.

Figure 2:
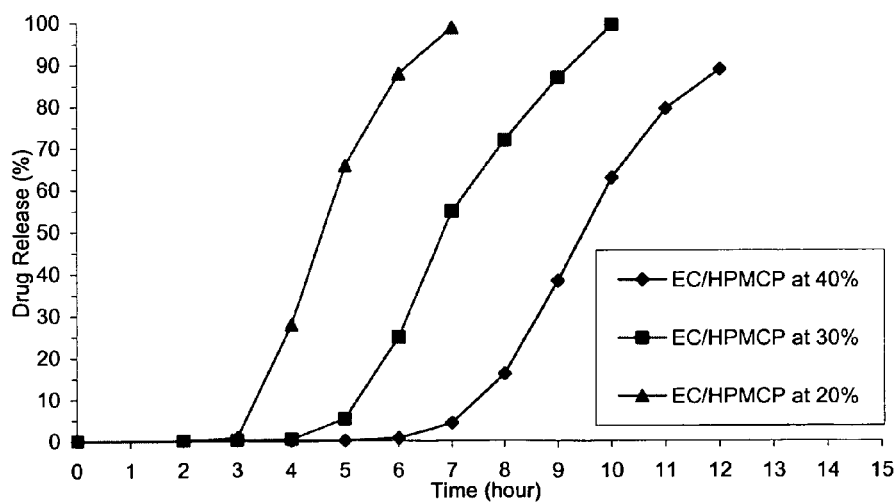
FIG. 2 shows drug-release profiles of propranolol hydrochloride IR beads (without a barrier coating) coated with EC/HPMCP at 20, 30 and 40% by weight of Example 2C.
Figure 3:
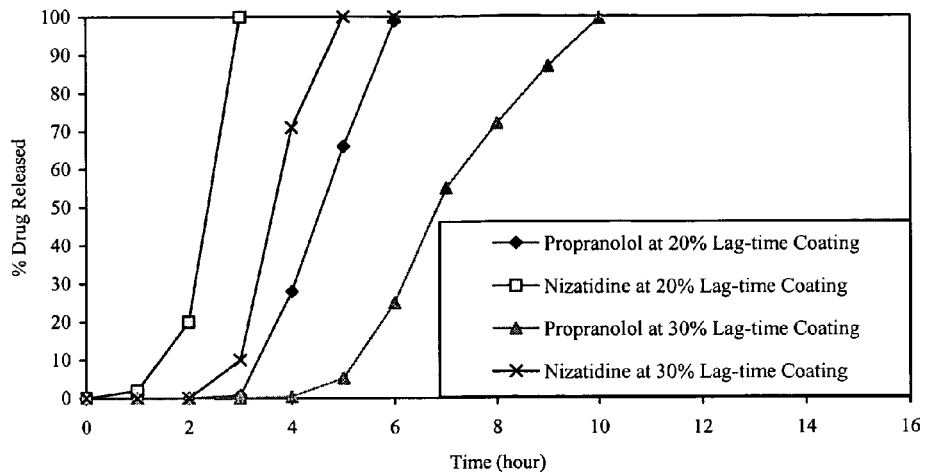
FIG. 3 shows drug release profiles of IR beads (without a barrier coating) coated with EC/HPMCP at 20% by weight (a) propranolol hydrochloride and (b) nizatidine and at 30% by weight (c) propranolol hydrochloride and (d) nizatidine.

Effect of Barrier-Coat on Lag-Time:

From a comparison of FIGS. 1 and 2, which depict the drug-release profiles of TPR beads without a barrier coat, it is clear that the TPR beads of nizatidine, a slightly alkaline drug, coated with EC/HPMCP at 30% by weight exhibits a lag-time of less than 3 hours. In contrast, the TPR beads of propranolol HCl, a slightly acidic drug, coated with the same polymer blend at the same coating thickness exhibits a lag-time of about 5 hours. From a comparison of the lag-times observed from Nizatidine and propranolol HCl TPR beads at identical coating conditions and compositions, it is evident that the acidity/alkalinity plays a major role in providing the lag time (FIG. 3).

Figure 4:
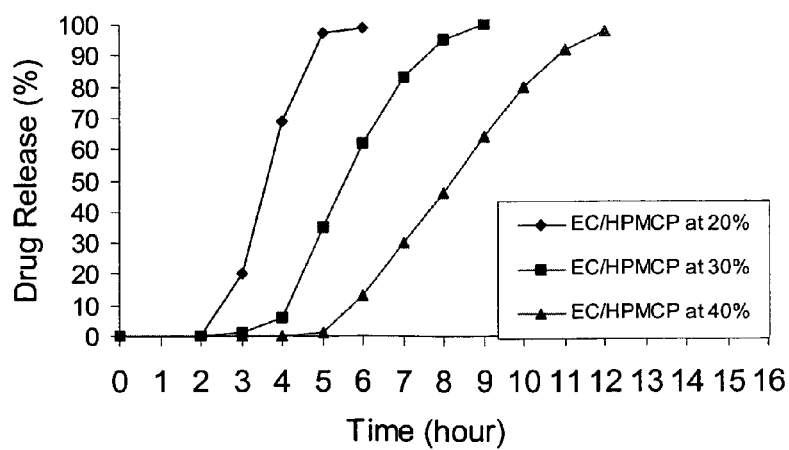
FIG. 4 shows drug release profiles of nizatidine IR beads coated first with a barrier coating of HPMCP and then coated with a lag-time coating at 20, 30 and 40% by weight of Example 1D.
Figure 5:
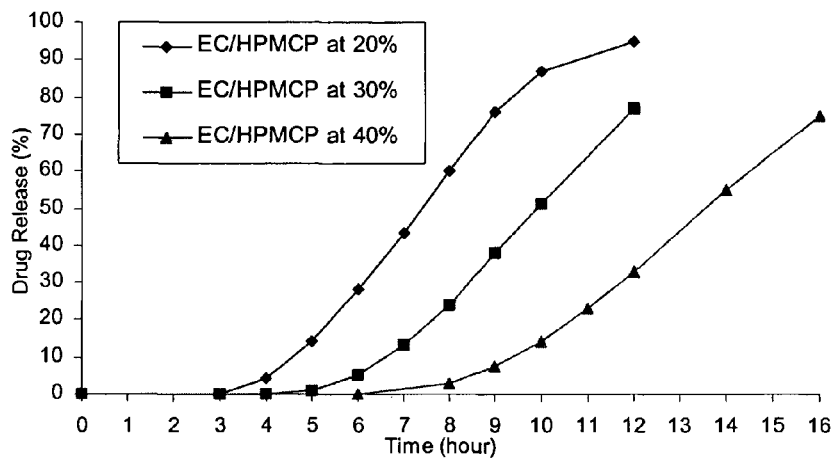
FIG. 5 shows drug release profiles of nizatidine IR beads coated first with a barrier coating of EC/HPC and then coated with a lag-time coating at 20, 30 and 40% by weight of Example 1E.
Figure 6:
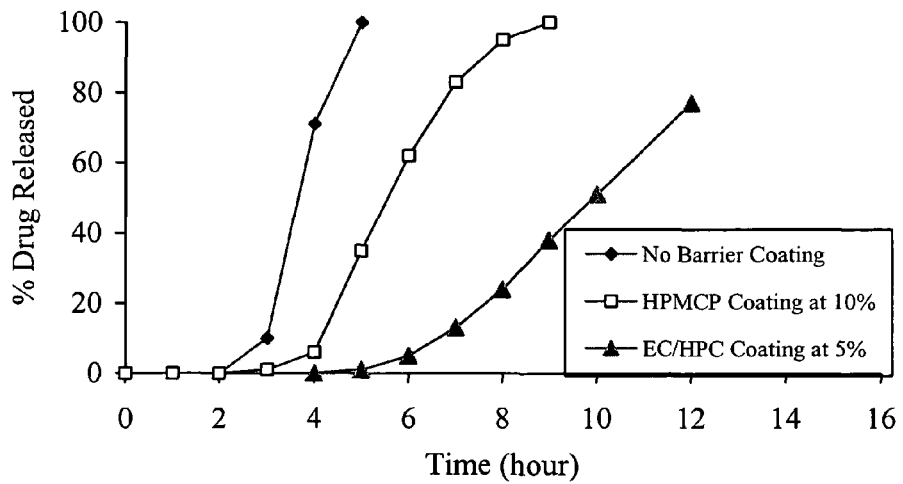
FIG. 6 shows the effect of the barrier coating applied on nizatidine IR beads on the lag time achieved at a lag-time coating of 30% by weight: (A) None, (B) 10% HPMCP and (C) 5% 70/30 EC/HPC.

FIGS. 4 and 5 demonstrate the effect of a barrier coating on the lag time that can be achieved for nizatidine beads. For example, at the coating of 40% by weight, an enteric-polymer barrier provides a lag time of about 5 hours while a more hydrophobic barrier of EC/HPC enables achieving a lag time of about 8 hours. These differences become clearer from FIG. 6, which shows the drug-release profiles from TPR beads at 30% coating: i) with no barrier coating; ii) with a barrier coating of an enteric polymer; or iii) a hydrophobic polymer blend. It is evident that a barrier coating with a hydrophobic water-insoluble polymer such as ethylcellulose provides longer lag times as compared to a barrier coating of an enteric polymer from TPR beads of alkaline drugs.

From these demonstrations, it is apparent that the alkalinity/acidity of the active pharmaceutical ingredient has a significant impact on the lag time that can be achieved at given coating conditions. Another active such as atenolol which is more alkaline than nizatidine would be expected to show shorter lag time than nizatidine. Of course, the lag time can be increased by providing a barrier coating comprising an appropriate polymer alone or in combination with a membrane modifier (for example, hydrophobic ethylcellulose alone or together with water-soluble hydroxypropylcellulose). The membrane thickness can be varied to further fine-tune the lag time.

While the invention has been described in detail and with respect to specific embodiments thereof, it will be apparent that numerous modifications and variations are possible without departing from the scope of the invention as defined by the following claims.

What is claimed is:

1. A pharmaceutical composition comprising one or more populations of timed, pulsatile release beads, wherein at least one population of timed, pulsatile release beads comprises:
   a) a core particle comprising an acidic active pharmaceutical ingredient or a pharmaceutically acceptable salt thereof;
   b) an inner barrier coating comprising a water insoluble polymer in combination with a water-soluble/pore-forming polymer; and
   c) an outer lag-time coating comprising a water-insoluble polymer in combination with an enteric polymer
   wherein the at least one population of timed, pulsatile release beads provides a lag time greater than 6 hours before onset of drug release when tested using USP Apparatus 1 or 2 and a two-stage dissolution medium (first two hours in 700 mL of 0.1N HCl and thereafter in 900 mL at pH 6.8).

2. The pharmaceutical composition of claim 1, wherein said acidic active pharmaceutical ingredient when suspended in purified or de-ionized water at a drug content of 1 g/ml or more exhibits a more acidic pH compared to that of the de-ionized water, and is selected from the group consisting of analgesics, anticonvulsants, antidiabetic agents, anti-infective agents, antineoplastics, anti-Parkinsonian agents, antirheumatic agents, cardiovascular agents, central nervous system stimulants, dopamine receptor agonists, anti-emetics, gastrointestinal agents, psychotherapeutic agents, opioid agonists, opioid antagonists, anti-epileptic drugs, histamine $H_2$ antagonists, anti-asthmatic agents, and skeletal muscle relaxants and mixtures thereof.

3. The pharmaceutical composition of claim 1, comprising two or more timed, pulsatile release bead populations to provide target pharmacokinetic profiles suitable for a once or twice-daily dosing regimen.

4. A pharmaceutical dosage form comprising the composition of claim 1.

5. The pharmaceutical composition of claim 1, wherein said core particle comprises:
   i) an inert particle coated with said acidic active pharmaceutical ingredient and optionally a polymeric binder; or
   ii) a pellet, or mini- or micro-tablet, a microgranule, or a granular particle containing said acidic active pharmaceutical ingredient.

6. The pharmaceutical composition of claim 5, wherein said polymeric binder is selected from the group consisting of polyvinylpyrrolidone, methylcellulose, hydroxypropylcellulose, hydroxypropyl methylcellulose, corn starch, pregelatinized starch, and mixtures thereof.

7. The pharmaceutical composition of claim 1, wherein said enteric polymer is selected from the group consisting of cellulose acetate phthalate, hydroxypropyl methylcellulose phthalate, hydroxypropyl methylcellulose succinate, polyvinyl acetate phthalate, pH-sensitive methacrylic acid-methylmethacrylate copolymers, shellac, and mixtures thereof.

8. The pharmaceutical composition of claim 1 wherein said inner barrier coating comprises from about 1.5% to 20% by weight of the barrier coated bead.

9. The pharmaceutical composition of claim 1, wherein the ratio of said water insoluble polymer to said enteric polymer in said outer lag-time coating ranges from about 10:1 to 1:3.

10. The pharmaceutical composition of claim 1 wherein said water-insoluble polymer is selected from the group consisting of ethylcellulose, cellulose acetate, cellulose acetate butyrate, polyvinyl acetate, methylmethacrylate ester polymers, neutral copolymers based on ethylacrylate and methylmethacrylate, copolymers of acrylic and methacrylic acid esters, and mixtures thereof.

11. The pharmaceutical composition of claim 1, wherein at least one of the inner barrier coating and the outer lag-time coating comprises a plasticizer.

12. The pharmaceutical composition of claim 1, wherein the ratio of said water insoluble polymer to enteric polymer in said outer lag-time coating ranges from approximately 3:1 to approximately 1:1.

13. The pharmaceutical composition of claim 1, further comprising immediate release beads, each immediate release bead comprising a core particle comprising said acidic active pharmaceutical ingredient or a pharmaceutically acceptable salt thereof;
wherein said immediate release beads release not less than about 90% of said acidic active pharmaceutical ingredient contained therein within the first hour after oral administration of the dosage form.

14. The pharmaceutical composition of claim 1, further comprising (1) a second population of timed, pulsatile release beads, or (2) a population of immediate release beads, or (3) a second population of timed, pulsatile release beads and a population of immediate release beads,
wherein said first and second timed, pulsatile release bead populations exhibit different release characteristics.

15. The pharmaceutical composition of claim 1, wherein said outer lag-time coating comprises ethylcellulose in combination with hydroxypropyl methylcellulose phthalate.

16. A method for preparing the pharmaceutical composition of claim 1, the method comprising:
a) preparing immediate-release beads comprising an acidic active pharmaceutical ingredient or a pharmaceutically acceptable salt thereof;
b) applying an inner barrier coating on said immediate release beads, said inner barrier coating comprising a water-insoluble polymer in combination with a water-soluble/pore-forming polymer c) applying an outer lag-time coating comprising a water-insoluble polymer in combination with an enteric polymer onto inner barrier coated beads of step b) or onto said immediate-release beads of step a) to form a population of timed, pulsatile release beads; and
d) combining one or more populations of timed, pulsatile release beads and immediate release beads in the form of a capsule or a tablet.

17. The method of claim 16, further comprising:
e) incorporating said timed, pulsatile release beads into a pharmaceutical dosage form.

18. A method of treating a disease or medical condition comprising administering to a patient in need thereof the composition of claim 1.

19. A method comprising orally administering to a patient the pharmaceutical composition of claim 1 wherein said composition comprises a population of immediate-release beads and one or more populations of timed, pulsatile release beads comprising one or more acidic active pharmaceutical ingredients.

20. The pharmaceutical composition of claim 1, wherein the ratio of said water insoluble polymer to said enteric polymer in said outer lag-time coating ranges from about 10:1 to 1:2.

21. The pharmaceutical composition of claim 1, wherein the amount of said outer lag-time coating is about 20% to 60% by weight of said timed, pulsatile release bead.

22. The pharmaceutical composition of claim 14, comprising an immediate-release bead population and two timed, pulsatile release populations, wherein the ratio by weight of the immediate release bead population to the first timed, pulsatile release bead population to the second timed, pulsatile release bead population ranges from about 10/20/70 to about 30/60/10.

23. The pharmaceutical composition of claim 14, wherein said pharmaceutical composition takes the form of a capsule, a conventional tablet, or an orally disintegrating tablet.

24. The pharmaceutical composition of claim 1, wherein said outer lag-time coating consists essentially of a water-insoluble polymer in combination with an enteric polymer.

25. The method of claim 16, wherein said outer lag-time coating consists essentially of a water-insoluble polymer in combination with an enteric polymer.

26. The pharmaceutical composition of claim 1, wherein the amount of said outer lag-time coating is about 1.5% to 60% by weight of said timed, pulsatile release bead.

27. The pharmaceutical composition of claim 1, wherein the lag time is about 7 hours.

28. The pharmaceutical composition of claim 1, wherein the lag time is about 8 hours.

29. The pharmaceutical composition of claim 1, wherein the lag time is about 9 hours.

30. The pharmaceutical composition of claim 1, wherein the lag time ranges from greater than 6 hours to about 9 hours.

31. A pharmaceutical dosage form comprising the pharmaceutical composition of claim 13.

32. The pharmaceutical dosage form of claim 31, comprising more than one acidic active pharmaceutical ingredient.

33. The pharmaceutical composition of claim 14, wherein the first population of timed, pulsatile release beads exhibits a lag time greater than 6 hours, and the second population of timed, pulsatile release beads exhibits a lag time of about 3 to about 5 hours.

34. The pharmaceutical composition of claim 33, comprising more than one active pharmaceutical ingredient.

35. The pharmaceutical composition of claim 14, comprising a first population of timed, pulsatile release beads and a second population of timed, pulsatile release beads, wherein the first and second timed, pulsatile release bead populations exhibit different release characteristics.

36. The pharmaceutical composition of claim 35, comprising more than one active pharmaceutical ingredient.

37. The pharmaceutical composition of claim 14, comprising a first population of timed, pulsatile release beads and a population of immediate release beads, wherein said composition comprises more than one active pharmaceutical ingredient.

38. The pharmaceutical composition of claim 14, comprising a first population of timed, pulsatile release beads and a second population of timed, pulsatile release beads and a population of immediate release beads, wherein the first and second timed, pulsatile release bead populations exhibit different release characteristics.

39. The pharmaceutical composition of claim 38, comprising more than one active pharmaceutical ingredient.

40. A pharmaceutical dosage form comprising the composition of claim 14.

41. The pharmaceutical composition of claim 1, comprising the inner barrier coating.

42. The pharmaceutical composition of claim of claim 41, wherein said water-soluble/pore-forming polymer is selected from the group consisting of polyvinylpyrrolidone, methylcellulose, hydroxypropylcellulose, hydroxypropyl methylcellulose, polyethylene glycol, and mixtures thereof.

* * * * *